United States Patent
Wisnewski et al.

[11] Patent Number: 5,562,663
[45] Date of Patent: Oct. 8, 1996

[54] IMPLANT INTERCONNECTION MECHANISM

[75] Inventors: Paul J. Wisnewski, Cordova, Tenn.; Roger P. Jackson, Prairie Village, Kans.

[73] Assignee: Danek Medical, Inc., Memphis, Tenn.

[21] Appl. No.: 482,835

[22] Filed: Jun. 7, 1995

[51] Int. Cl.$^6$ ............................ A61B 17/70; A61B 17/86
[52] U.S. Cl. ............................................ 606/61; 606/73
[58] Field of Search .......................... 606/61, 60, 69, 606/70, 71, 72, 73

[56] References Cited

U.S. PATENT DOCUMENTS

| | | |
|---|---|---|
| 4,887,596 | 12/1989 | Sherman . |
| 5,005,562 | 4/1991 | Cotrel . |
| 5,067,955 | 11/1991 | Cotrel . |
| 5,154,719 | 10/1992 | Cotrel . |
| 5,217,497 | 6/1993 | Mehidan ............................. 606/61 |
| 5,257,993 | 11/1993 | Asher et al. . |
| 5,261,907 | 11/1993 | Vignaud et al. . |
| 5,346,493 | 9/1994 | Stahurski et al. . |
| 5,380,326 | 1/1995 | Lin . |
| 5,496,321 | 3/1996 | Puno et al. .......................... 606/61 |

*Primary Examiner*—Michael Powell Buiz
*Assistant Examiner*—Scott B. Markow
*Attorney, Agent, or Firm*—Woodward, Emhardt, Naughton, Moriarty & McNett

[57] ABSTRACT

Spinal implants with features for anchorage in or onto bone or to connectors, have a body with an upwardly opening channel receiving a spinal rod therein. The channel has sidewalls with a curved slot in each of the sidewalls. A cap is mounted on the implant body and has a central portion received in the channel and has tongues at each side of the central portion, the tongues being received in the curved slots in the sidewalls. A set screw threaded into the cap engages the spinal rod and clamps the rod between the body and the set screw and fixes the cap to the body. The curved slots enable installation of the cap in minimal space measured lengthwise of the rod. Each implant body has an integral bone screw, or bone hook, or lateral connector rod or parallel spinal rod receiving body thereon.

39 Claims, 11 Drawing Sheets

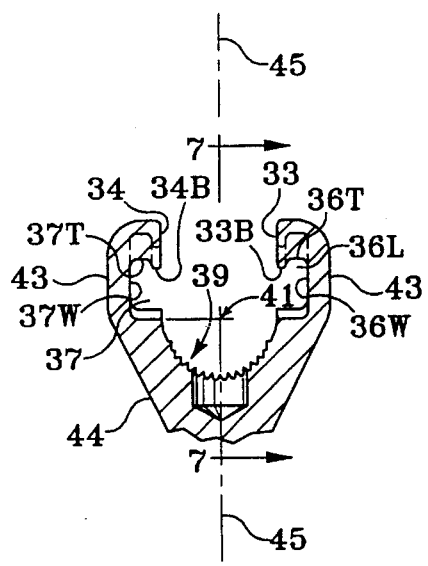
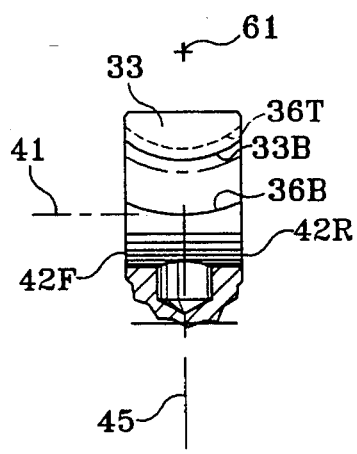
Fig. 6        Fig. 7
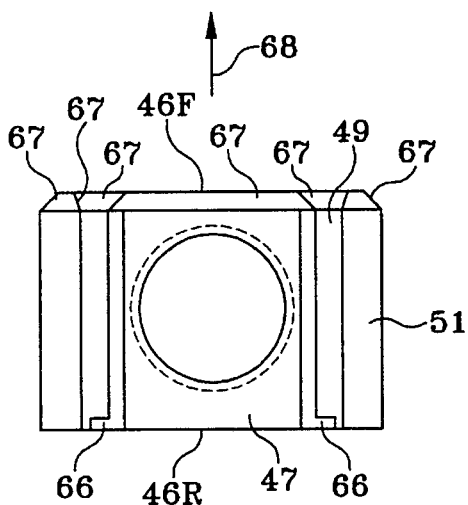
Fig. 8
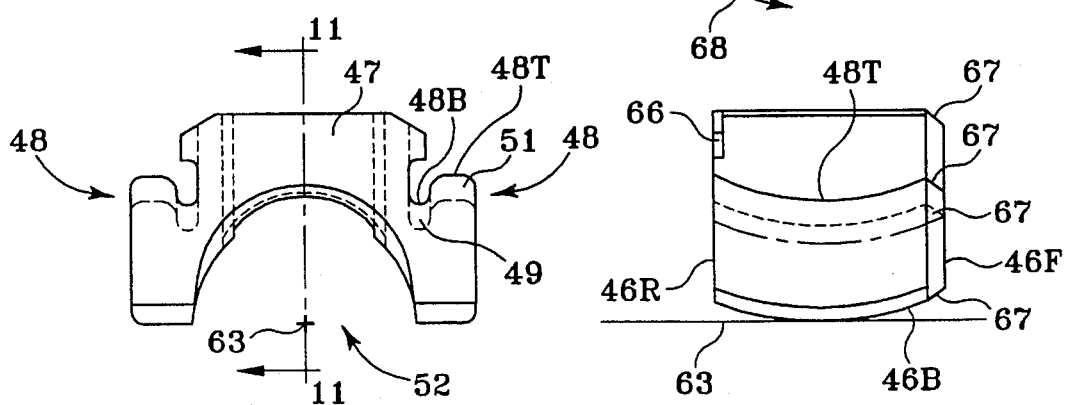
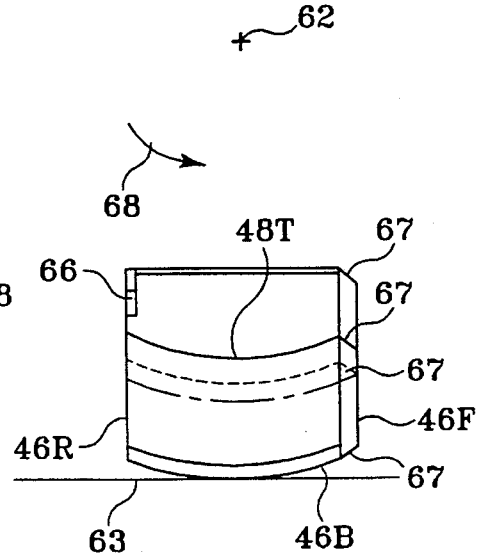
Fig. 9        Fig. 10

97 98 99

IMPLANT INTERCONNECTION MECHANISM

BACKGROUND OF THE INVENTION

1. Field of the Invention

This invention relates generally to spinal osteosynthesis and more particularly, to a system for making connections from various types of anchors to the spinal rods themselves.

2. Description of the Prior Art

Many types of hooks and screws and rods and connectors have been devised for use in connection with spinal osteosynthesis. U.S. Pat. No. 5,005,562 issued Apr. 9, 1991 to Yves Cotrel shows examples of all of these devices. It shows screws 19 including the "threaded rod" portion 21 anchored in bone, and hooks 18 including the curved blade portion 1 hooked around bone. It also includes transverse rods 22 with hooks 23 on them and set screws for clamping the hooks 20 and 23 to the spinal rods. Some such devices use screws and hooks which must be slided onto the end of the spinal rod for installation. In the Cotrel patent, the hooks and screws are "top opening" and have, for example, a body 2 with two "side branches" 4 and defining between them a channel 6 with a rounded bottom 7 to receive the spinal rod 3 between them. A plug 8 is screwed into the thread 11 formed in the inner walls of the branches 4, thereby closing the channel after insertion of the spinal rod from the top, and having either a center point 12 or peripheral ring 13 or both projecting downward from the face of the plug to penetrate and lock on the spinal rod when the plug is tightened in the channel. A sawtooth thread pitch on the screw is used to avoid spreading the branches as the plug is tightened.

The type of hook and screw head shown in and described in the Cotrel patent, where the spinal rod can be inserted directly from above into the receiving channel is in a category referred to as an "open system", in contrast to the necessity in certain other systems for introducing the spinal rod to the hook or screw axially or endwise of the rod through an aperture in the hook or screw and then clamping them. U.S. Pat. No. 5,261,907 issued Nov. 16, 1993 to Vignaud et al. is another example of spinal rods anchored in open-headed pedicular screws secured to the rod by a locking screw 6, with annular element 9 around the diapason-shaped cylindrical head 5 and element 9 locked in place around the "branches" 5a and 5b of head 5 by the tendency of the branches to spread as the screw 6 tends to spread the branches. There has remained a need for a system using open screws and hooks secured to the spinal rods, easily fixable in position by the use of a set screw, but without the need for some kind of special threads for the set screw or some ring or other arrangement capturing the branches of the screw head. The present invention is addressed to that need.

SUMMARY OF THE INVENTION

Described briefly, in a typical embodiment of the present invention, implants are provided for osteosynthesis, and have features for anchorage in or onto bone or to connectors. As applied to spinal osteosynthesis, the implants have a body with an upwardly opening channel receiving a spinal rod therein. The channel has sidewalls with a curved slot in each of the sidewalls. A cap is mounted on the implant body and has a central portion received in the channel and has tongue portions at each side of the central portion, the tongue portions being received in the curved slots in the sidewalls. A fastener mounted in the body or cap clamps the rod, the body and cap together. The curved slots enable installation of the cap in minimal space measured lengthwise of the rod. The implant body has an integral bone screw, or bone hook, or lateral connector rod or parallel spinal rod receiving body thereon.

BRIEF DESCRIPTION OF THE DRAWINGS

FIG. 6 is a section through the top portion of the screw taken at line 6—6 in FIG. 3 and viewed in the direction of the arrows.

FIG. 7 is a section therethrough taken at line 7—7 in FIG. 6 and viewed in the direction of the arrows.

FIG. 8 is a top plan view of one embodiment of a cap for the screw of FIG. 2.

FIG. 9 is a rear elevational view thereof.

FIG. 10 is a side elevational view thereof.

DESCRIPTION OF THE PREFERRED EMBODIMENT

Figure 1:
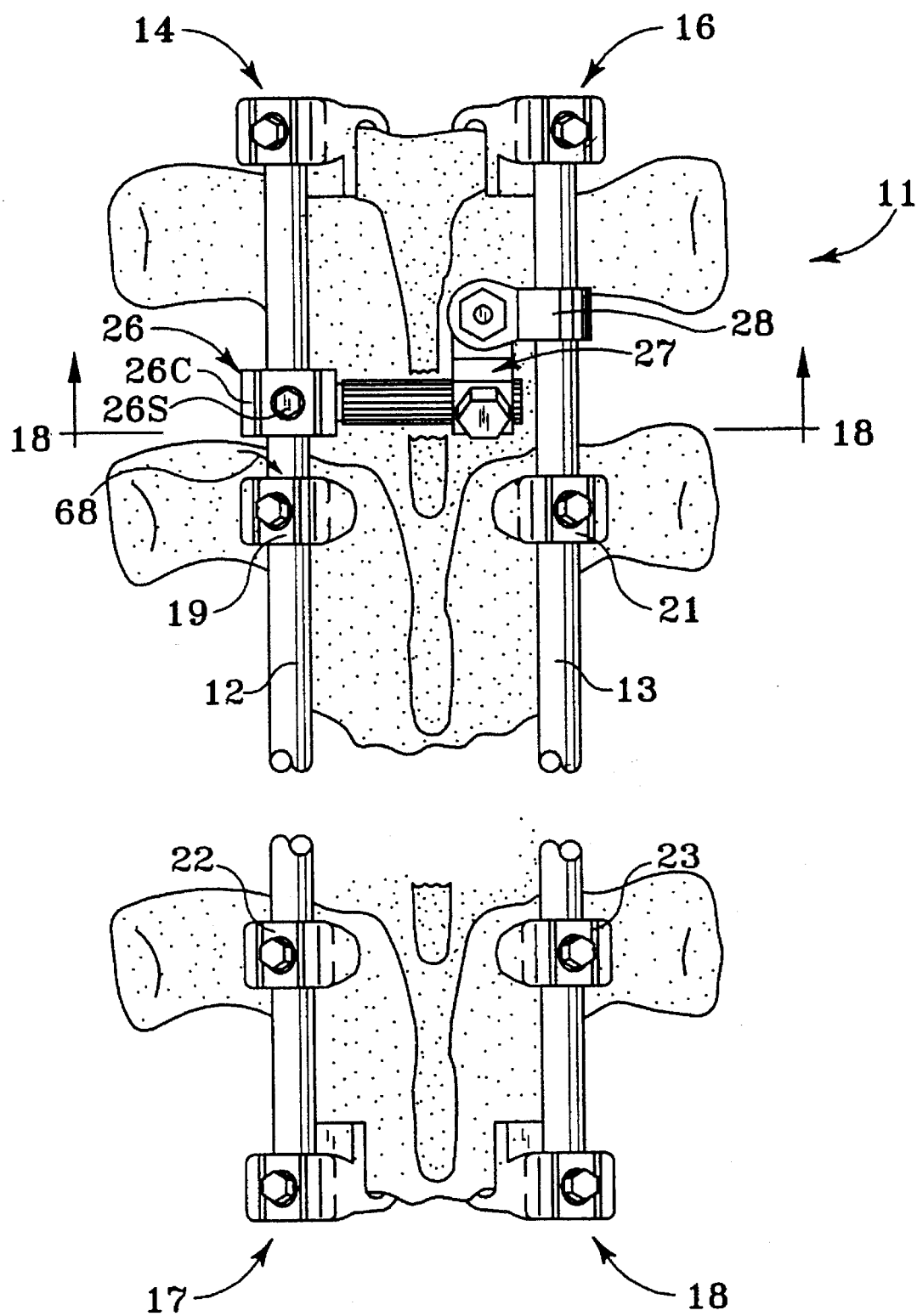
FIG. 1 is a schematic view of a portion of the spine with an osteosynthesis system applied thereto incorporating implants according to the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings in detail, in FIG. 1 there is a spinal column shown generally at 11 with an osteosynthesis system including two spinal rods 12 and 13 and, for purposes of illustration, two supralaminar hook assemblies 14 and 16, two infralaminar hook assemblies 17 and 18 and four screw assemblies 19, 21, 22 and 23. There is also a lateral connector assembly 26 and associated connectors 27 and 28. The screws and hooks are used for the same types of purposes as described in the above-mentioned Cotrel patent, but have some advantages.

FIGS. 2 through 7 show one of the screw assemblies such as 19. It includes a body portion 31, having an upwardly opening U-shaped slot 32 therein which serves as a spinal rod receiver channel. Each of the channel sidewalls 33 and 34 has a curved slot such as 36 and 37, respectively, therein. The slot is L-shaped, with the "leg" portion 36L of slot 36 cooperating with the channel wall 33 to form a downwardly extending flange whose lower edge 33B cooperates with the bottom 36B of slot 36 to form the "foot" of the L-shape.

The bottom 39 of the rod receiver channel is curved about a longitudinal axis 41 of the channel and has ridges therein parallel to the axis 41.

Figure 2:
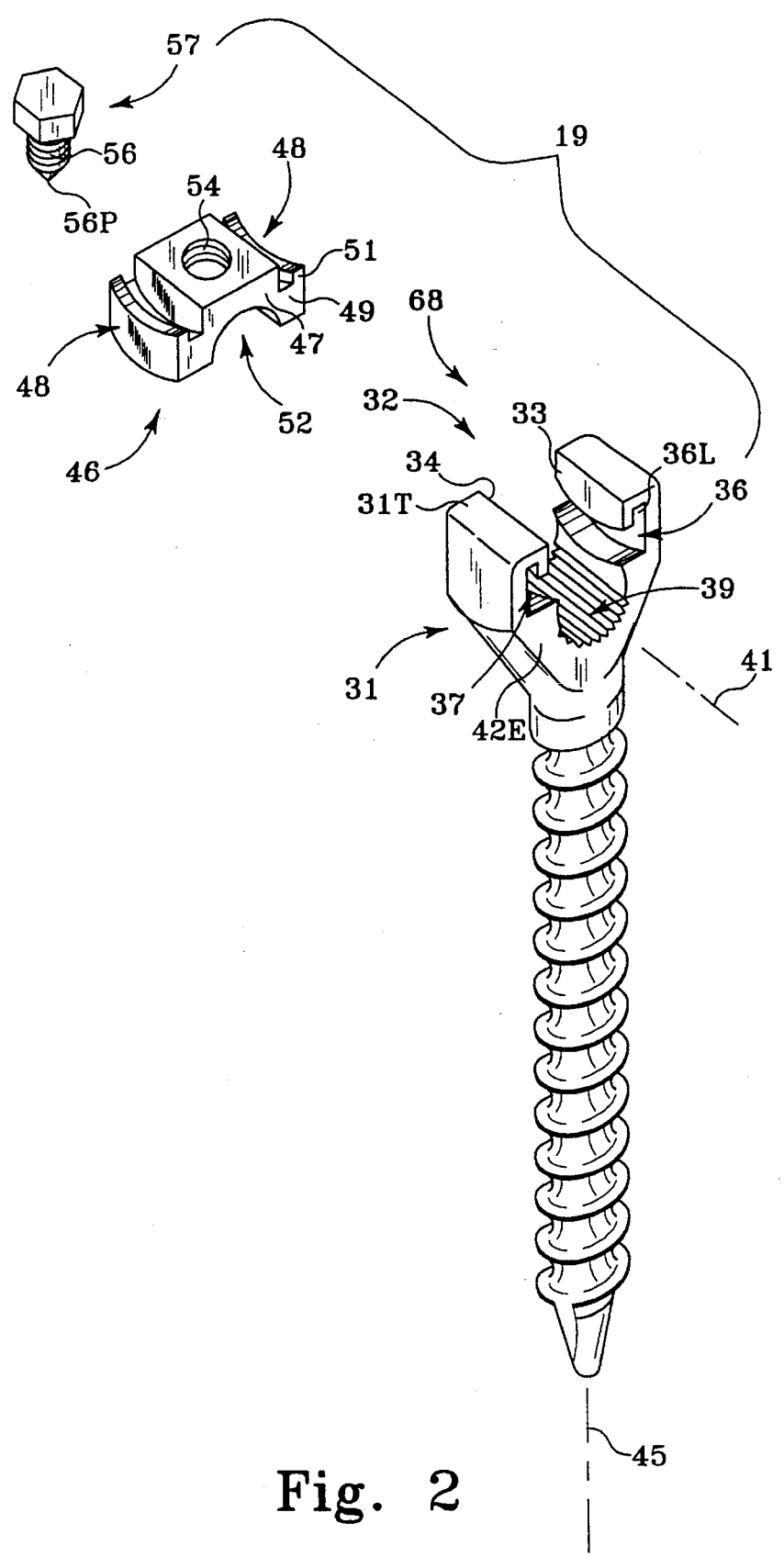
FIG. 2 is a perspective view of three parts of a screw and cap type of implant assembly according to the present invention.
Figure 3:
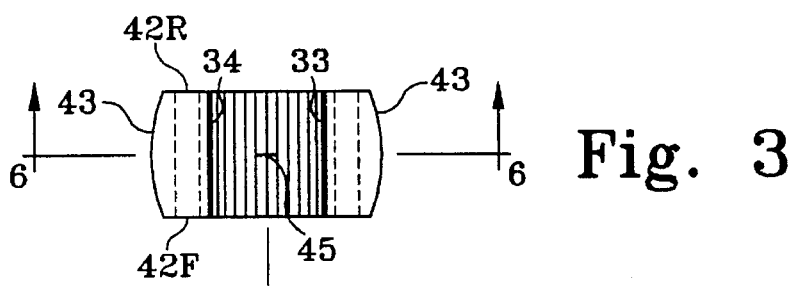
FIG. 3 is a top plan view of the screw itself.
Figure 4:
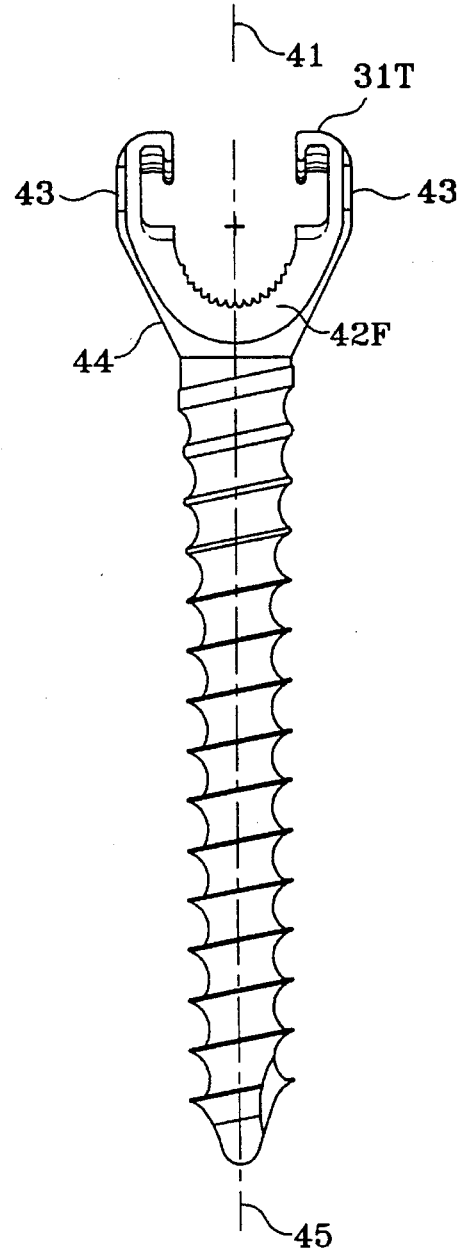
FIG. 4 is a front elevational view thereof.
Figure 5:
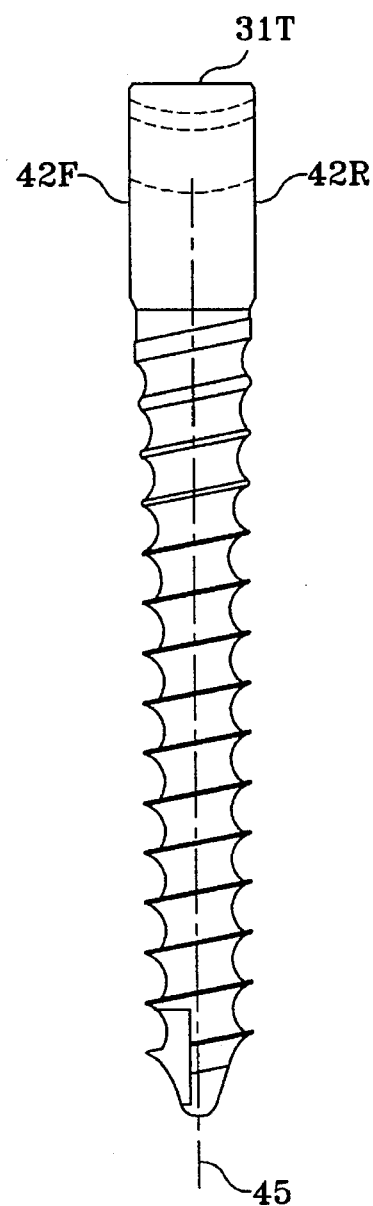
FIG. 5 is a side view thereof.

The body of the screw has parallel flat front and rear faces such as 42F and 42R being in planes at a spacing of about 7.00 mm and perpendicular to the channel axis 41. As best seen in FIGS. 2 and 3, the upper portions of the body at the sides 43 of the flat faces 42F and 42R are curved, the maximum outside dimension being about 13 mm, for example. The sides 43 blend into a conical portion 44 providing the transition from the faces and sides of the body to the threaded stem whose longitudinal axis 45 is perpendicular to axis 41 and centered between faces 42F and 42R. The screw is threaded for anchoring in bone and has a self-tapping point.

The cap 46 FIGS. 2 and 8–12 has a central portion 47 and outwardly extending curved flange or tongue portions 48 at each side of the central portion. These flange or tongue portions are generally L-shaped in having a foot portion 49 and leg portion 51. The bottom of the central portion of the cap has a downwardly opening rod-receiving channel 52. Threaded aperture 54 receives the threads 56 of the socket head cap screw 57 which serves as a set screw in the assembly, fastening the rod to the pedicle screw and cap assembly.

Referring again specifically to FIGS. 4, 6 and 7, the L-shaped slots face each other and, as best shown in FIG. 7, the bottom 36B of the foot portion of the slot is curved about an axis 61 which is above the channel bottom cylindrical axis 41 and lies in a plane that is perpendicular to the channel bottom cylindrical axis 41 and lies in a second plane that is perpendicular to the screw axis 45. Similarly, the bottom 33B of the downwardly projecting flange of channel face 33 is curved about the axis 61. So is the top 36T of the downwardly opening leg portion 36L of the channel formed by the flange. For a pedicle screw in which the radius from the axis 41 to the rod-engaging channel bottom grooves is about 3.25 mm, the radius from axis 61 to the flange bottom 33B is about 5.8 mm and to the bottom 36B of the slot 36 is about 8.9 mm, for example.

Referring again to FIGS. 8–12, these show that the top 48T of each of the tongues is curved about an axis 62 which is in a plane that is centered between the front and rear faces 46F and 46R of the cap and perpendicular to the center line 63 of the cap which is also the center line of the rod receiving channel 52 therein. The bottom 46B of the cap is also curved about the same center. So is the bottom 48B of the slot formed by the tongue 48. These features are slidingly fittable in the mating features of the screw in a tongue-in-groove relationship. An abutment stop ear 66 is provided on each side of the central portion of the cap at the rear face 46R thereof and near the top of the cap. Chamfers 67 are provided at all outside edges of the front face of the cap. These features facilitate insertion of the cap into the top of the bone screw in the direction of arrow 68 in FIGS. 1, 2, 8 and 10, for example. Engagement of the stop ears 66 with the rear face 42R of the screw, will prevent the cap from sliding all the way through the channel and out.

Figure 11:
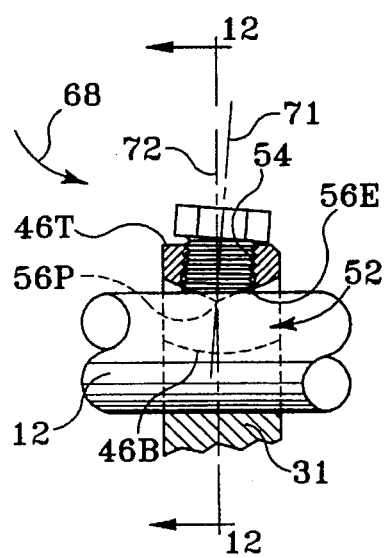
FIG. 11 shows a section of the cap taken at line 11—11 in FIG. 9 and viewed in the direction of the arrows but installed with a spinal rod and pedicle screw shown in section.
Figure 12:
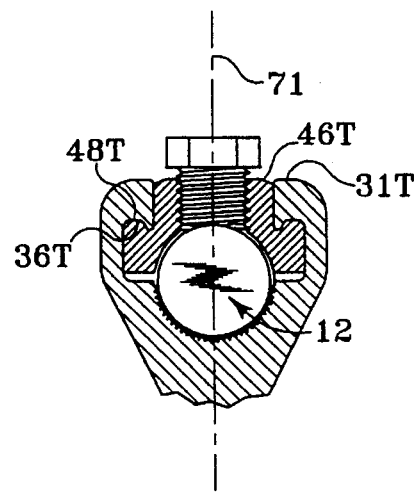
FIG. 12 shows a section taken at line 12—12 in FIG. 11 and viewed in the direction of the arrows.
Figure 13:
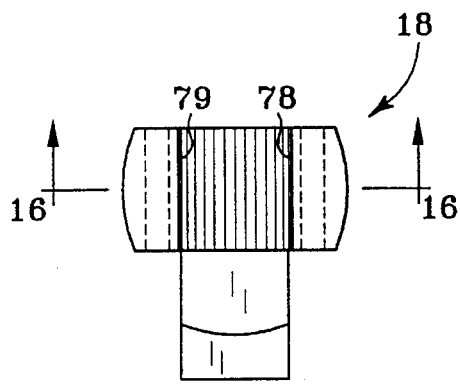
FIG. 13 is a top plan view of a hook incorporating the present invention.
Figure 14:
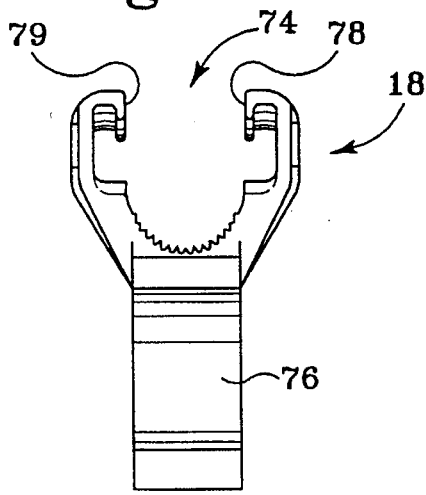
FIG. 14 is a front elevational view thereof.
Figure 15:
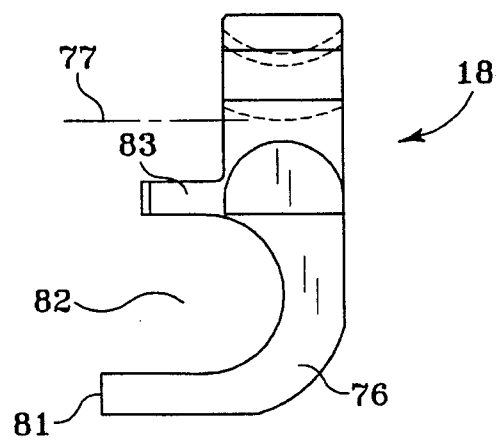
FIG. 15 is a side elevational view thereof.
Figure 16:
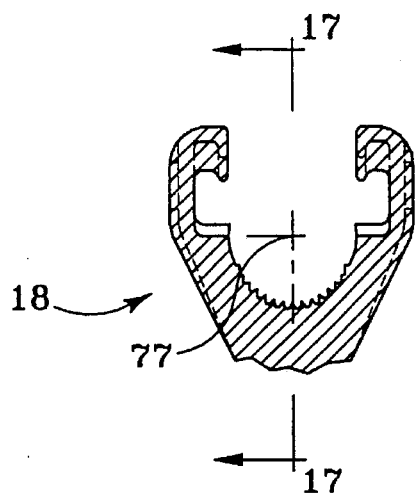
FIG. 16 is a section through the top portion thereof taken at line 16—16 in FIG. 13 and viewed in the direction of the arrows.
Figure 17:
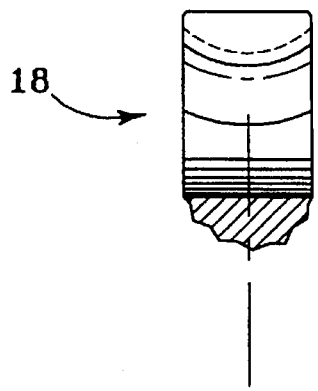
FIG. 17 is a section therethrough taken at line 17—17 in FIG. 16 and viewed in the direction of the arrows.

Referring now to FIG. 11, note that the axis 71 of the threaded aperture 54 is at a 10° angle with respect to the vertical center line 72 of the cap. This enables not only the point 56P at the bottom of the set screw to bite into and anchor the rod 12, but enables also the edge 56E of the set screw to bite into and lock against the rod. This not only drives the rod tightly against the grooves in the bottom of the channel in the pedicle screw, but also drives the cap up to snug engagement of the tongue top portions 48T with the tops such as 36T of the grooves or L-shaped slots in the screw. At the same time, the top 46T of the cap is at the same essentially flush level as the top 31T of the screw body, thus minimizing the overall height of the system.

FIGS. 13–17 show an infralaminar hook such as 18 in FIG. 1 and in which all features are the same as for the screw in FIGS. 1–7 except that, instead of having the threaded stem, the hook 18 has a curved blade 76 extending down from the rod receiving channel body portion 74 thereof. The center line 77 of the curve of the channel bottom lies in a vertical plane that is the center of the part, being equi-distant from the channel side flanges 78 and 79. The blade 76 is also centered with respect to this plane. The blade extends generally in this plane in the direction of the center line 77 and the particular shape of the channel 82 in the blade may be dictated by the application such as whether it is to be an infralaminar hook, a supralaminar hook, a pedicular hook, or a thoracic hook, for example. For the infralaminar hook, a pad 83 is provided in vertically spaced relation to the lower portion of the blade to provide a distinct U-shaped channel for reception on bone.

The configuration of the curved, L-shaped slots, the channel bottom grooves and other features of the hook which receive the spinal rod and the cap, are the same as for the pedicular screw described above and the rod is assembled into the hook or vice-versa in the same manner from the top as for the screw, followed by installation of the cap in the same manner as described above with reference to the pedicular screw.

Figure 18:
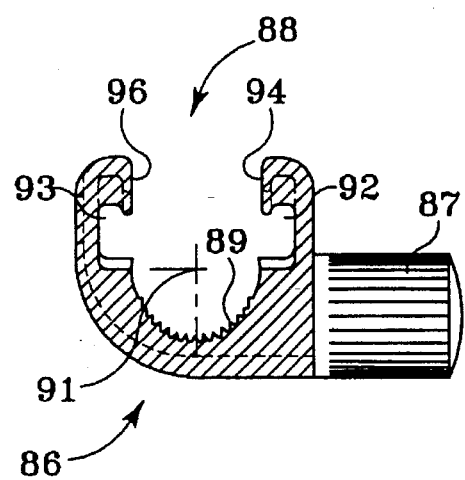
FIG. 18 is a view of a lateral connector taken at line 18—18 in FIG. 1 and viewed in the direction of the arrows.
Figure 19:
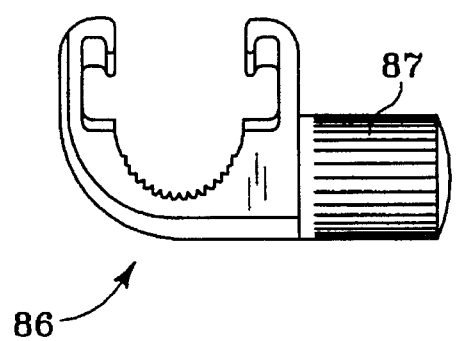
FIG. 19 is a front elevational view of that connector.

Referring now to FIGS. 18 and 19, a part of the lateral connector assembly 26 of FIG. 1 is shown. It includes the body portion 86 and lateral rod portion 87. The body portion has the U-shaped upwardly-opening spinal rod receiver channel 88, with the curved bottom portion 89 having its longitudinal center line 91 which, in the assembly, is the center of the spinal rod 12. The channel sides have the curved L-shaped slots 92 and 93 formed by the downwardly projecting flanges 94 and 96 which are the sides of the channel 88. These features are the same as described above with reference to the pedicle screw and receive the cap 26C and set screw 26S (FIG. 1) in the same manner as described above for the pedicle screw and cap and set screw assembly 19. The rod 87 extending laterally from the body portion is useful for making a connection to the other spinal rod through a swivel base clamp 27 and U-clamp 28, or other types of clamps to the respective rod 87 and spinal rod 13, but which are not parts of the present invention and need not be further described. The rod portion 87 of the assembly 18 can be made of any length (long as in FIG. 1, to short as in FIG. 18) desired for the intended purpose, as well as having the longitudinal ridges or teeth in the number, nature and extent desired to inhibit rotation of the clamp such as 27 attached to it.

Figure 20:
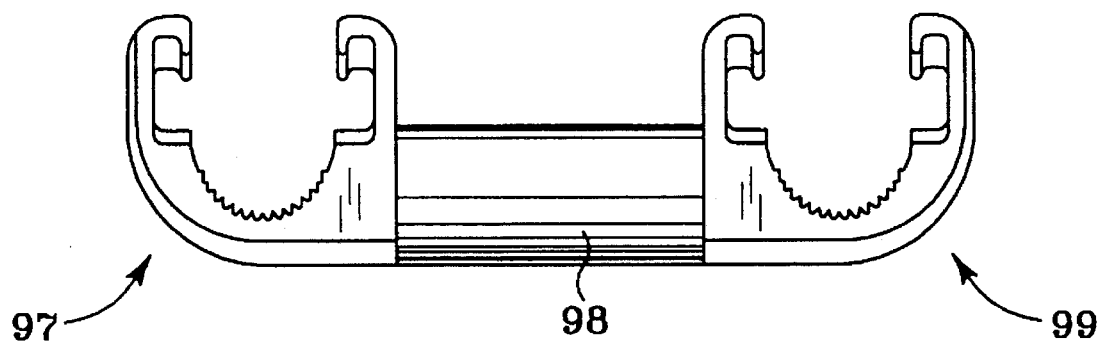
FIG. 20 is a front elevational view of a lateral connector similar to that of FIGS. 18 and 19 but having two rod-receiving channels therein.

FIG. 20 shows a lateral connector of the same nature as in FIG. 19. For example, the body portion 97 thereof is exactly the same as body portion 86 of FIG. 19. But instead of a rod such as 87 being used to receive a clamp on it, the integral rod 98 can be a smooth rod with an integral body portion 99 at the right-hand end thereof, having exactly the same features as the body portion 97. Consequently, where the spinal rods call be spaced a known desired dimension apart, or where there is a need to space a couple of rods a predetermined known distance apart, this particular embodiment of the invention can be used with the rods, caps and set screws mounted and secured in the same manner as described above with reference to the other embodiments.

Figure 21:
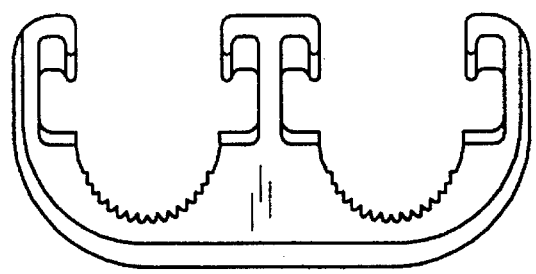
FIG. 21 is a front elevational view of a lateral connector like that in FIG. 20, except that there is no transverse rod between the channels.

FIG. 21 shows an embodiment of the invention in which there are two body portions joined together in a Siamese twin arrangement without the intermediate lateral rod portion 98 of the FIG. 20 embodiment. The rod receiver channel and curved slot portions are the same in size and configuration as described above with reference to the FIGS. 3–7 embodiment, and the spinal rod or other rods can be installed therein in the same manner as described above.

Figure 22:
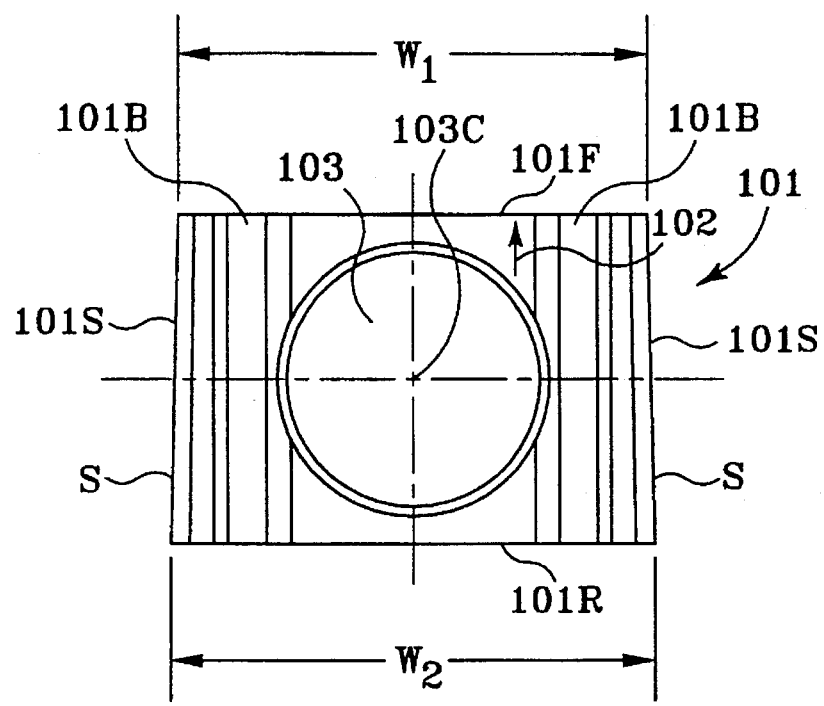
FIG. 22 is a top plan view of a preferred embodiment of a cap for the screw of FIG. 2.
Figure 23:
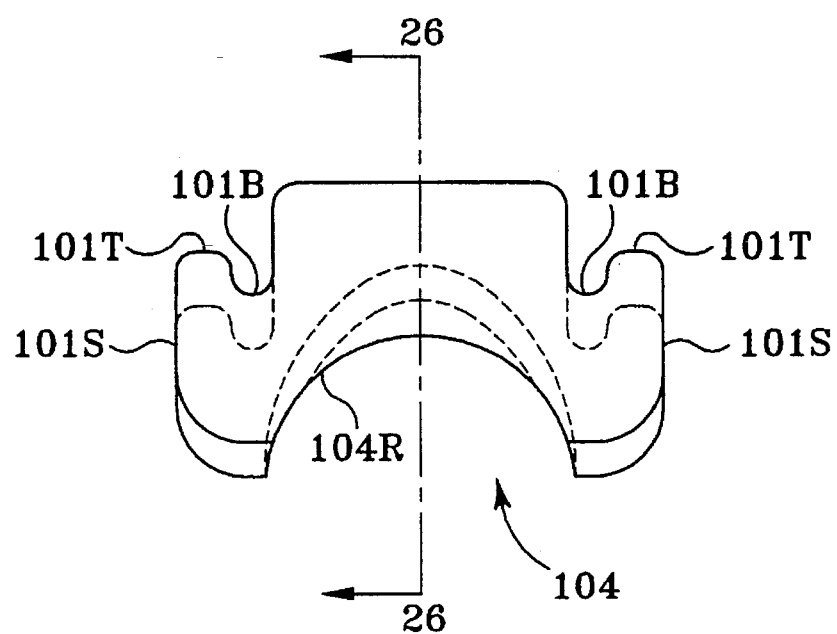
FIG. 23 is a rear elevational view thereof.
Figure 24:
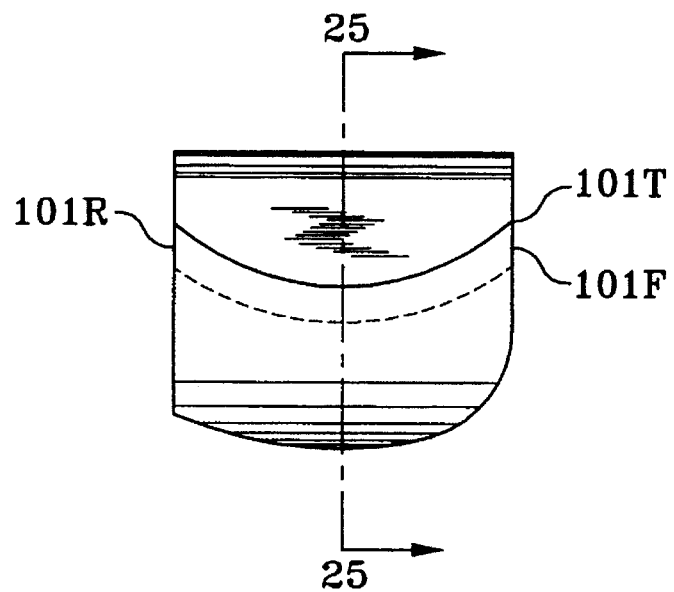
FIG. 24 is a side elevational view thereof.
Figure 25:
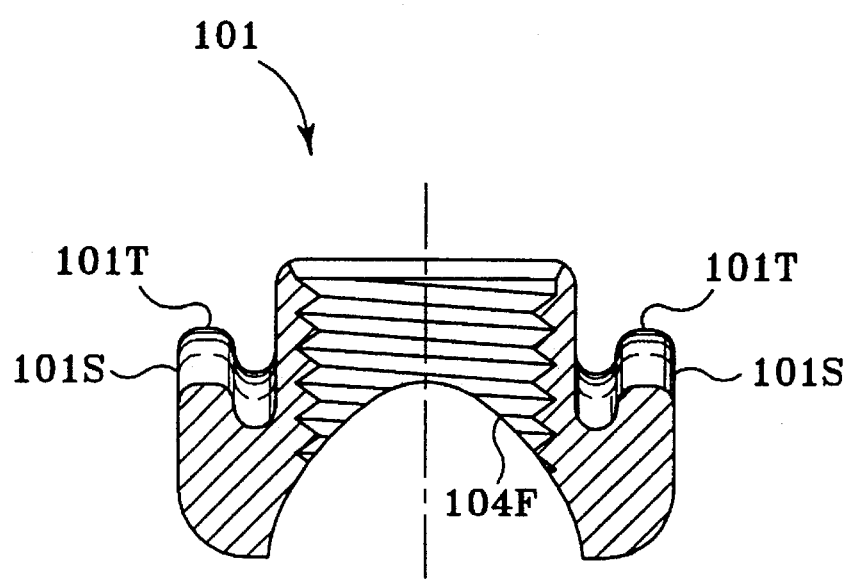
FIG. 25 is a section taken through the cap on lines 25—25 in FIG. 24 and viewed in the direction of the arrows.

Referring now to FIGS. 22 through 27, these show a preferred embodiment of the cap for use with the pedicle screw of FIGS. 2–7, 11–12 and with the various other rod-receiving implants of FIGS. 1 and 13–21. In this case, instead of the cap having the stop ears 66, the cap 101 has other features that prevent it from being pushed too far into or entirely through the upwardly-opening channel in the body portion of the implant. Referring specifically to FIG. 22, which is the top view, the cap has a front or leading edge 101F and a rear or trailing edge 101R. It has the sides 101S which diverge slightly so that the overall width $W_1$ at the leading edge is slightly less than the overall width $W_2$ at the trailing edge. For example, if the overall width at the leading edge is 10.1 mm, the overall width at the trailing edge can be 10.4 mm. In this example, where the overall length between the leading edge 101F and trailing edge 101R is 7.00 mm, the width increases from the leading edge to 10.4 mm at a vertical line S at each side and located 5.75 mm back of the leading edge. Therefore, there is no taper in the sides 101S from line S to the trailing edge 101R.

With the slots in the sides of the U-shaped channel having straight walls from the front to the rear, the cap will become snug in the slots when it is installed in the direction of arrow 102 (engraved in the top of the cap) to the point where the center 103C of the set screw thread aperture 103 is 1.25 mm away from colinearity with the center line 45 of the screw. A pliers or crimping tool can be used to advance the cap the rest of the way to colinearity of the set screw aperture axis with the pedicle screw axis.

Figure 26:
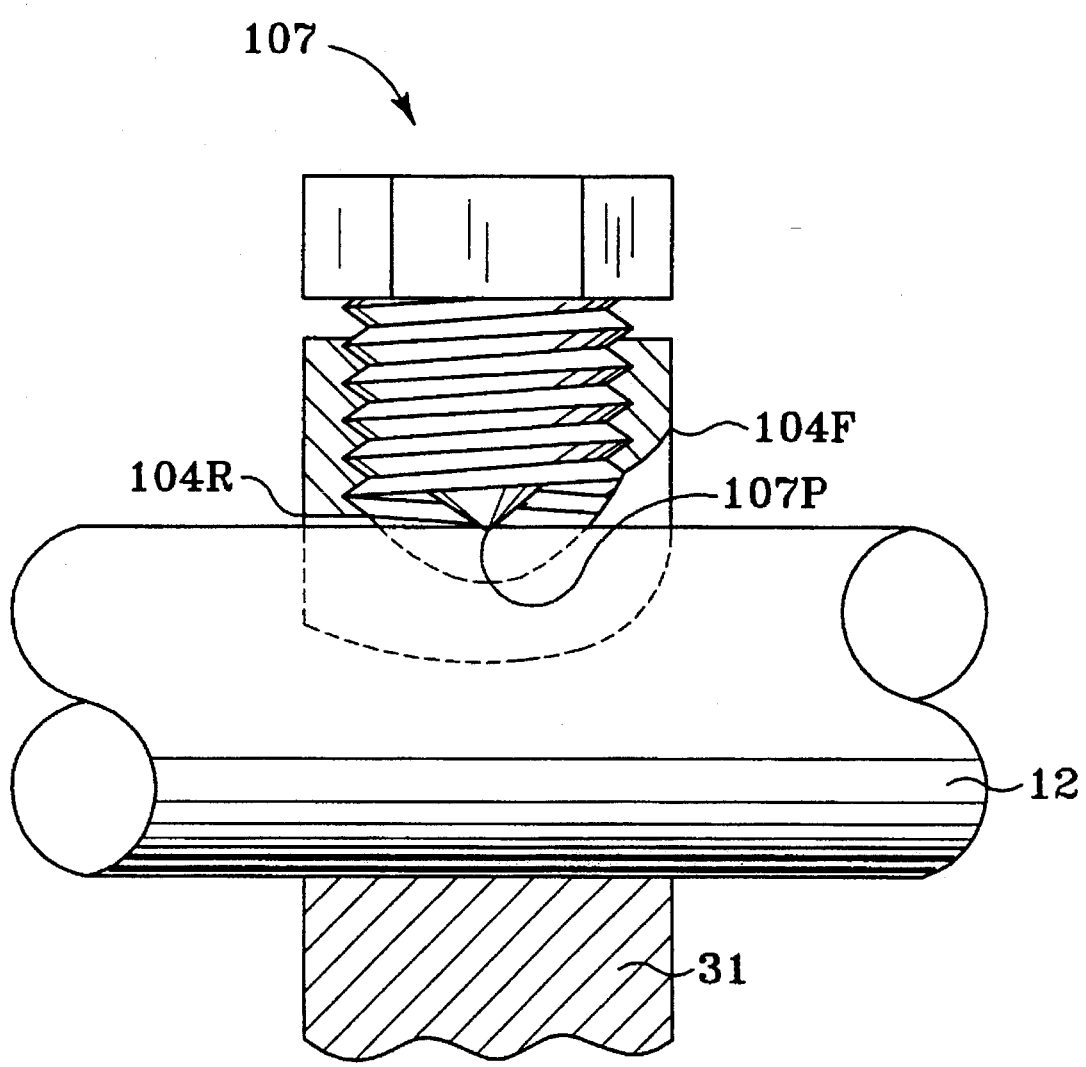
FIG. 26 shows a section of the cap taken at line 26—26 in FIG. 23 and viewed in the direction of the arrows, but installed with a spinal rod and with a pedicle screw shown fragmentarily and in section.
Figure 27:
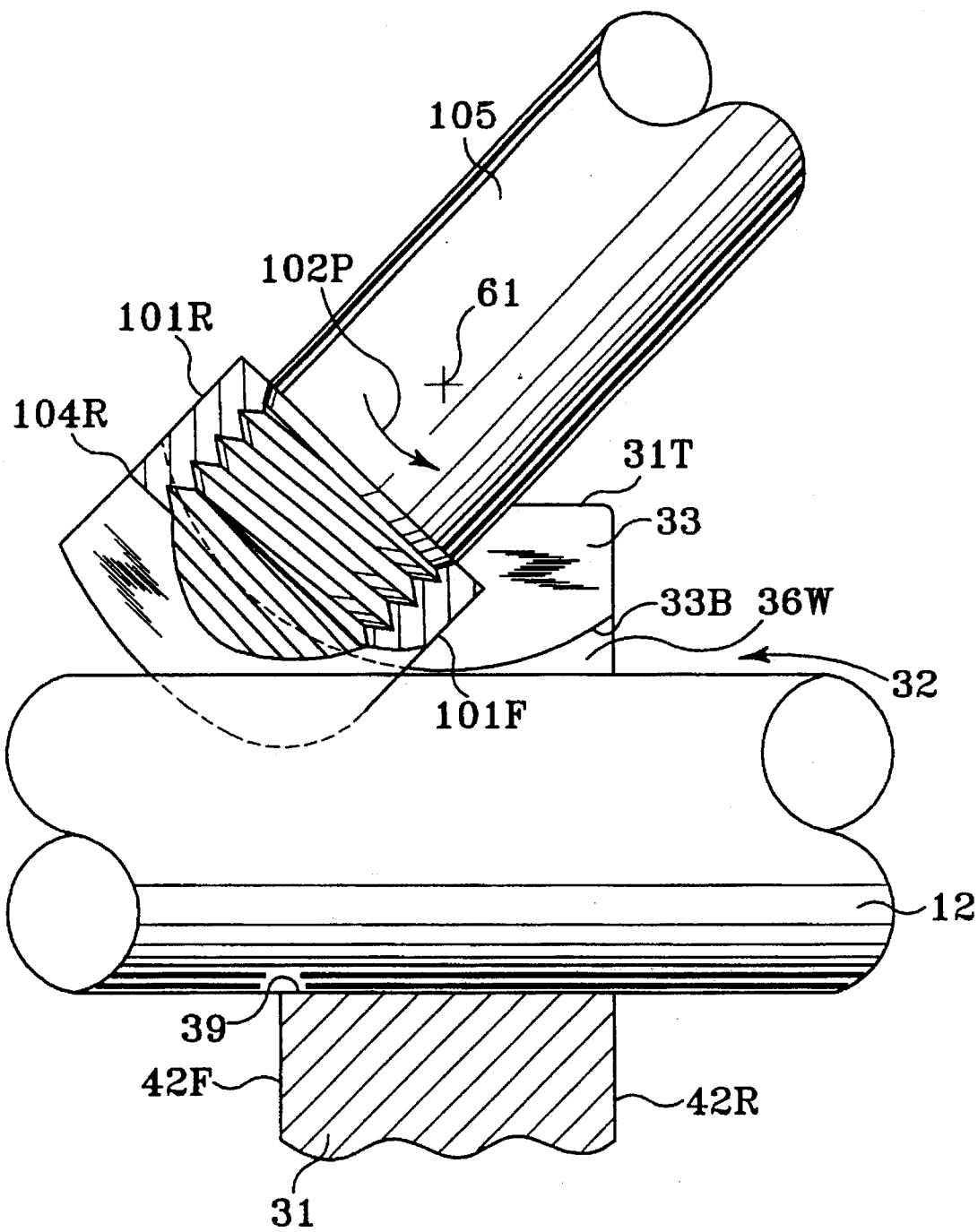
FIG. 27 is a view like FIG. 26 but showing the manner of insertion of the cap into the pedicle screw before securing the set screw in the cap.

In this embodiment of the cap, the shapes of the intersections of the downwardly opening channel 104 with the leading and trailing edges of the cap, are different from each other. Note in FIG. 23, for example, that the shape 104R at the trailing edge is basically the same as for the cap in FIG. 9. But in the section shown in FIG. 25, it is apparent that the shape at the leading edge as defined by the high arched edge 104F is different from the shape 104R at the trailing edge in FIG. 23. The reason for the change in contour of the channel from the rear edge 104R to the front edge 104F can be best understood by referring to FIGS. 26 and 27. In FIG. 27, the spinal rod 12 is in place on the bottom 39 of the rod receiver channel. Installation of the cap is achieved by first installing the threaded lower end of a manipulating tool 105 into the set screw thread aperture 103. Then the cap is tilted so that the leading edge 101F is down near the top of the spinal rod 12 so that the groove bottoms 101B (FIGS. 22 and 23) of the cap will be received under the flange edges 33B, 34B (FIGS. 6 & 7), and the tongue rail tops 101T (FIG. 25) at the front of the cap will be received in the grooves such as 36L (FIG. 6) immediately under the top 36T of the groove in the slots 36 at both sides of the channel 32, whereupon the cap can be moved into position through the arcuate path 102P (FIG. 27) into the position shown in FIG. 26. When the cap has reached the position shown in FIG. 26, where the leading and trailing faces 101F and 101R of the cap are co-planar with the faces of the screw body 31, the sides 101S of the cap, particularly behind the lines S, will have become wedged against the vertically extending walls 36W and 37W of slots 36 and 37 at the front face 42F of the body portion of the screw. When the cap is in this attitude as shown in FIG. 26, the installation tool 105 is removed and the set screw 107 is installed and can be turned down so that the point thereof 107P engages and embeds to the extent desired or needed in the top of the rod 12. As the screw is tightened, the bottoms 101B of the grooves and tops 101T of the rails in the cap will abuttingly engage the bottoms of the flanges 33 and 34 of the body portion of the screw and the tops 36T and 37T of the slots 36 and 37, respectively, in the mounting screw 31. Consequently, the assembly of the spinal rod, mounting screw 31, cap 101 and set screw 107 will remain permanently and securely in place thereafter. The rear edge 104R of the channel 104 will be closely spaced to the top of the rod as shown in FIG. 26. It may be recognized that, even if the wedging function did not occur, as the cap is turned into place in the direction of arrow 102P, rear edge 104R and the top of the downwardly opening rod receiving channel 104 behind the set screw aperture will come down onto the spinal rod and prevent further advance of the cap in the rod receiving channel 32 of the screw, as the cap is confined by the curved bottoms such as 33B of the side flanges cooperating with the upwardly opening curved grooves in the cap, and the tops 101T of the curved rails in the cap cooperating with the curved tops 36T of the slots 36, dictating the arcuate movement of the cap as it is installed.

All of the components for the various embodiments of the invention can be made of a material such as 316L ASTM F138 Grade 2 Cold Rolled 900/1050 MPa material. Other materials may also be found suitable. Also, although some specific dimensions were given above with respect to examples, the invention is not limited to those particular sizes. The devices can be used with smooth surface rods or rods having knurled or diamond embossed surfaces. The present invention has significant advantages over known prior art. Among these are minimal volume requirements, but convenience in use. The tongue-in-groove relationship of cap to slot avoids concern about spreading of branches of a diapason-type head and avoids the need for any bulky girdling closure to control such spreading. The tongue-in-groove arrangement with curved slots enables installation of the cap in less space between implants situated along a spinal rod than is possible with other arrangements which require caps to be installed by motion precisely parallel to the rod axis and thus require more space between implants along the rod. The lateral stop ears on the FIG. 8–12 embodiment prevent loss of control of the cap during installation, and facilitate initial location of it in place. The angled set screw axis enables at least two-point engagement of the set screw with the spinal rod and in a direction tending to push the cap tight against the slots in the screw or hook or lateral connector, as the case may be, while, at the same time, urging the cap stop ears in a direction tending to pull the cap tight against the implant body portion in a direction lengthwise of the rod receiver channel axis. In the FIGS. 22–27 embodiment, the taper at the sides and the curved slots and channel opening shape at front and rear facilitate installation of the cap in one direction and appropriately limit its travel. The construction of both embodiments avoids the need for some over-cap arrangement which would not only be bulky, but also would tend to interfere with the use of other features or accessories in an osteosynthesis system, the lateral connector rod being just one example.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An osteosynthesis implant comprising:

a body with a generally U-shaped upwardly opening channel for receiving a shaft, and having a channel axis, the channel defined by first and second sidewalls and a bottom wall and open at the top, the channel having a first end and a secondary end;

a slot in each of the sidewalls extending between the first end and the second end of the channel and being curved in a plane generally parallel to a plane containing the channel axis and extending from said bottom wall through said open top;

a cap having a central portion received in the channel and having tongues at each side of the central portion, the tongues being received in the curved slots in the sidewalls; and a fastener in the cap and operable to clamp said shaft between the body and the cap to fix the shaft to the implant.

2. The implant of claim 1 and wherein:

the fastener is a set screw threaded into the cap and forcing said shaft received in the channel against the channel bottom, with portions of the tongues abuttingly engaging portions of the slots and thereby affixing the cap to the body and the body to the shaft.

3. The implant of claim 1 and wherein:

each of the curved slots has an L-shaped cross section in a plane perpendicular to the slots having an upstanding leg portion extending from the sidewall and a laterally extending foot portion extending from the leg portion, with the foot portion of the L on the first sidewall of the channel facing the foot portion of the L on the second sidewall of the channel.

4. The implant of claim 3 and wherein:

each of the tongues has an L-shaped cross section in a plane perpendicular to the tongues with a foot portion extending outward from the central portion of the cap and with a leg portion extending upward from the foot portion, and the leg portions of the tongues are received in the leg portions of the slots in the body channel sidewalls.

5. The implant of claim 4 and wherein:

the foot portions of the tongues are received in the foot portions of the body channel sidewall slots.

6. The implant of claim 1 and further including said shaft and wherein:

the channel bottom wall has said shaft thereon;

the cap has a downwardly-opening channel therein for cooperation with the upwardly-opening channel of the body and receiving said shaft therein; and the cap central portion has laterally extending stop ears engageable with the body to limit movement of the cap in the body.

7. The implant of claim 1 and further comprising:

a threaded stem integral with the body for anchorage in bone.

8. The implant of claim 7 and wherein:

the stem has a longitudinal axis which extends in a direction downward from the bottom wall of the channel.

9. The implant of claim 8 and wherein:

the fastener has a longitudinal axis;

the channel bottom wall is generally semi-cylindrical, having a longitudinal cylindrical axis; and the stem axis and fastener axis are colinear in a plane containing the cylindrical axis.

10. The implant of claim 8 and wherein:

the fastener has a longitudinal axis;

the bottom wall of the channel is generally semi-cylindrical, having a longitudinal cylindrical axis; and the stem axis and fastener axis lie in a plane containing the cylindrical axis, the stem axis and fastener axis converging at an angle of less than 15° and intersecting at a point near a top of the cap central portion.

11. The implant of claim 8 and wherein:

the bottom of the channel is generally semi-cylindrical, having a longitudinal axis;

the body has parallel flat outer faces at the first and second ends of the channel, and located in planes perpendicular to the channel axis; and the body has cylindrical outer faces intercepting the flat faces, the cylindrical outer faces being centered in a plane containing the axis of the stem.

12. The implant of claim 11 and wherein:

the space between the planes of the faces is less than the distance between the cylindrical faces.

13. The implant of claim 12 and wherein:

the space between the planes of the faces is about half the distance between the cylindrical faces.

14. The implant of claim 1 and wherein:

the channel axis is a first axis to orient the shaft coaxially with the channel, and each of the slots has a bottom surface that is curved about at least one second axis that is above the first axis and lies in a first plane that is perpendicular to the first axis.

15. The implant of claim 14 and wherein:

at least one slot has a top surface that is curved about the second axis.

16. The implant of claim 14 and wherein:

the cap tongues have bottom surfaces curved about an axis above the cap bottom surfaces. 17. The implant of claim 16 and wherein:

at least one of the cap tongues has a top surface engageable with the top surface of said at least one slot. 18. The implant of claim 17 and wherein:

the cap tongues have upstanding rails with top surfaces curved about an axis above said cap tongue top surfaces of the rails. 19. The implant of claim 17 and wherein:

the cap has front and rear faces; and the cap tongue portions bottom surfaces are curved about multiple axes parallel to the second axis. 20. The implant of claim 1 and wherein:

the curved slot in each of the sidewalls provides a downturned flange at each sidewall;

each of the tongues has an upstanding rail; and the flanges are received between the rails and central portion of the cap. 21. The implant of claim 20 and wherein:

the channel axis is a first axis to orient the shaft coaxially with the channel; and each of the flanges has a bottom surface that is curved about at least one second axis that is above the flange bottom surface and lies in a plane that is perpendicular to the first axis. 22. The implant of claim 21 and wherein:

the cap has an upwardly-opening groove between the central portion and each of the rails and which has a groove bottom which is curved about the second axis. 23. The implant of claim 22 and wherein:

the flange bottom surfaces are engageable with the groove bottoms. 24. The implant of claim 21 and further comprising:

a threaded stem integral with the body for anchorage in bone. 25. The implant of claim 21 and further comprising:

a rod integral with the body and extending laterally from the body. 26. The implant of claim 25 and wherein:

the integral rod has an axis perpendicular to a plane containing the first axis. 27. The implant of claim 26 wherein said body is a first body and further comprising:

a second body integral with the rod and spaced from the first body which is equivalent to the first body as set forth in claim 1. 28. The implant of claim 21 wherein said body is a first body and further comprising:

a second body integral with the first body and which is equivalent to the first body as set forth in claim 1. 29. The implant of claim 28 and wherein:

the channels of the first and second bodies have parallel axes to receive parallel shafts. 30. The implant of claim 21 and further comprising;

a hook integral with the body for hooking onto bone. 31. The implant of claim 30 and wherein:

the cap has front and rear faces;

the tongues have sides; and the overall width across the tongues adjacent the front faces is less than the overall width across the tongues adjacent the rear faces. 32. The implant of claim 31 and wherein:

the body has front and rear faces;

each of the slots has an outside wall at a predetermined spacing from the outside wall of the other slot; and the width across the tongues adjacent the front face is less than the said spacing, and the width across the tongues adjacent the rear face is at least as much as said spacing. 33. The implant of claim 32 and wherein:

the width across the tongues at locations on the sides of the tongues partway between the front and rear faces is the same as the width adjacent the rear faces. 34. The implant of claim 33 and wherein:

the said locations from the rear face are less than 20% of the distance from the rear face to the front face. 35. The implant of claim 31 and wherein:

the channel bottom has said shaft thereon;

the cap has a downwardly-opening channel therein for cooperation with the upwardly-opening channel of the body and receiving said shaft therein; and the cap channel has a semi-circular arched edge at the rear face of the cap, and the cap channel has an elongated arched edge at the front face of the cap enabling reception of the tongues at the front face of the cap in the slots when the cap is tilted during installation of the cap in the body with the said shaft on the channel bottom. 36. A method of securing a spinal rod to a spinal anchoring implant having an upwardly opening rod-receiving channel therein and comprising the steps of:

providing an implant having a channel defined by a bottom wall, first and second side walls, and an open top, and having first and second side slots in the first and second side walls, the slots each being curved in a plane generally parallel to a rod-receiving plane extending from the bottom wall of the channel to the top of the channel;

placing the spinal rod in the bottom of the channel;

taking an implant top cap having side tongues and tilting the cap with respect to the spinal rod and then inserting ends of the tongues of the cap into the channel side slots of the anchoring implant; and then advancing the cap longitudinally of the rod while advancing the tongues longitudinally in the slots and, simultaneously rocking the cap rearward in the curved slots as the cap is installed in the implant. 37. The method of claim 36 and further comprising the steps of:

wedging the cap tongues in the side slots as the cap is advanced to a final position in place in the implant. 38. The method of claim 37 and further comprising the step of:

before advancing the cap, threading a threaded end of a cap manipulating tool into a setscrew aperture in the cap, and then proceeding with the steps of tilting the cap and inserting the ends. 39. The method of claim 38 and further comprising the step of:

after advancing the cap to the final position in the implant, removing the tool from the setscrew receiver aperture;

installing a setscrew in the aperture; and driving the setscrew against the spinal rod and pulling the cap into tight engagement with the implant.

\* \* \* \* \*